(12) United States Patent
Kimura et al.

(10) Patent No.: US 8,318,739 B2
(45) Date of Patent: Nov. 27, 2012

(54) REMEDY FOR CORNEAL DISEASES

(75) Inventors: Takahito Kimura, Toyama (JP); Shigeto Fujishita, Toyama (JP); Hiroyoshi Kawada, Toyama (JP)

(73) Assignee: Teika Pharmaceutical Co., Ltd., Toyama-shi (JP)

( * ) Notice: Subject to any disclaimer, the term of this patent is extended or adjusted under 35 U.S.C. 154(b) by 0 days.

(21) Appl. No.: 12/828,420

(22) Filed: Jul. 1, 2010

(65) Prior Publication Data

US 2010/0267665 A1 Oct. 21, 2010

Related U.S. Application Data

(62) Division of application No. 12/064,408, filed as application No. PCT/JP2006/316550 on Aug. 24, 2006, now abandoned.

(30) Foreign Application Priority Data

Aug. 24, 2005 (JP) ................. 2005-242852

(51) Int. Cl.
*A01N 43/66* (2006.01)
*A61K 31/53* (2006.01)
(52) U.S. Cl. ..................... 514/245; 514/912
(58) Field of Classification Search ............ 514/245
See application file for complete search history.

(56) References Cited

U.S. PATENT DOCUMENTS

| 5,128,326 | A | * | 7/1992 | Balazs et al. | .............. | 514/54 |
| 7,129,243 | B2 | * | 10/2006 | Shima et al. | ............. | 514/252.03 |
| 2009/0030001 | A1 | | 1/2009 | Kimura et al. | | |
| 2010/0113456 | A1 | | 5/2010 | Kimura et al. | | |

FOREIGN PATENT DOCUMENTS

| JP | 55 313 | 1/1980 |
| JP | 3453152 B2 * | 10/2003 |
| WO | 99 40071 | 8/1999 |

OTHER PUBLICATIONS

Kato et al. (Treatment of branch retinal arterial occlusion with sodium ozagrel, a thromboxane A2 ozagrel, a thromboxane A2 synthetase inhibitor, Journal of international medical research Mar.-Apr. 1997;25(2):108-11).*
Voltaren Ophthalmic® (diclofenac sodium ophthalmic solution) 0.1% Sterile Ophthalmic Solution Rx only, Jul. 2009, 5 pages.
"Dexamethasone Sodium Phosphate Ophthalmic Solution, USP, Equivalent to dexamethasone phosphate 031% Sterile" Falcon Pharmaceuticals, Mar. 2006, 2 pages.
B.D. Srinivasan, "Corneal Reepithelialization and Anti-Inflammatory Agents", Tr. Am. Ophth. Soc. vol. LXXX, 1982, pp. 758-822.
Natsuko Hashizume, et al., "Effects of antiinflammatory drugs on migration of the rabbit corneal epithelium", J Cataract Refract Surg—vol. 27, Sep. 2001, pp. 1499-1502.
Amit G. Gupta, et al., "Effect of Inhibitors of Arachidonic Acid Metabolism on Corneal Reepithelialization in the Rat", Exp. Eye Res. (1993), 56, 701-708.
Takeshi Shimada, "Promoting Action of Eye Drops of Egualen Sodium for Regeneration of Corneal Epithelia in Model Rabbits where Corneal Epithelia were Mechanically Abraded", Doctoral thesis, chapter 4 section 2: Application of new chemical compound egualen sodium to eye drop., 1995, pp. 20-25 (w/English Translation).
Hironishi Inoue, "Thromboxane $A_2$ receptor antagonist", Faruaw, 32(10) 1221-1225, 1996 (w/English translation of boxed portion of p. 1225).
http://www.srf.or.jp/20nen/pdfs/20nen-data21.pdf Smoking Research Foundation, Kitsuen Kagaku Kenkyu No Ayumi (The history of smoking scientific research)—1996 to 2005- Compendium, Smoking and circulatory system (Kurahashi et al, Smoking and circulation : diversity of endothelium dependent contraction of artery induced by nicotine). (w/partial English of third page).
Joel G. Hardman, et al., "Regulation of Receptors", Pharmacodynamics, Goodman & Gilman's The Pharmacological Basis of Therapeutics, 1996, pp. 35-37.
http://database.japic.or.ip/pdf/newPINS/00057702.pdf Package Insert of Azuloxa Granules A therapeutic agent for gastric ulcer, Azuloxa®; Granules 2.5% (Egualen sodium hydrate formulation), 2010 (w/English Translation).
Pfister et al., (The effect of ophthalmic drugs, vehicles, and preservatives on corneal epithelium: a scanning electron microscope study, Investigative Ophthalmology & Visual Science, vol. 15, 246-259), Apr. 1976.
Arii et al., (The effect of ozagrel sodium on photochemical thrombosis in rat: Therapeutic window and combined therapy with heparin sodium Life Sciences vol. 71, Issue 25, Nov. 8, 2002, pp. 2983-2994).
Daniel, T.O., et al., "Thromboxane A2 is a Mediator of Cyclooxygenase-2-Dependent Endothelial Migration and Angiogenesis" Cancer Research, vol. 59, No. 18, 4574-4577, p. 4575, 1999.
Nian Xin Zheng, et al., "Pharmacokinetic and Pharmacodynamic Studies of a Thromboxane Synthetase Inhibitor, Ozagrel, in Rabbits", Biological and Pharmaceutical Bulletin, vol. 18, No. 12, XP-002569568, Dec. 1995, pp. 1738-1743.
Naveed B. K. Shams, et al., "Corneal Epithelial Cells Produce Thromboxane in Response to Interleukin 1 (IL-1)", Investigative Ophthalmology and Visual Science, vol. 27, No. 10, XP002569569, Oct. 1986, pp. 1543-1545.
Zheng Chen, et al., "Localisation of thromboxane $A_2$ receptors and the corresponding mRNAs in human eye tissue", The British Journal of Ophthalmology, vol. 78, No. 12, XP002569570, Dec. 1994, pp. 921-926.
M. L. Schwartzman, "Thromboxane in ocular pathophysiology", The British Journal of Ophthalmology, vol. 78, No. 12, XP 009129827, Dec. 1994, pp. 886-887.
Thomas O. Daniel, et al., "Thromboxane $A_2$ is a Mediator of Cyclooxygenase-2-dependent Endothelial Migration and Angiogenesis", Cancer Research, vol. 59, No. 18, Sep. 15, 1999, pp. 4574-4577.

* cited by examiner

*Primary Examiner* — Sreeni Padmanabhan
*Assistant Examiner* — Layla Soroush
(74) *Attorney, Agent, or Firm* — Oblon, Spivak, McClelland, Maier & Neustadt, L.L.P.

(57) ABSTRACT

The present invention provides a method for treating a corneal disease by administering to a patient in need of such treatment an effective amount of ozagrel or a salt thereof.

17 Claims, No Drawings

REMEDY FOR CORNEAL DISEASES

TECHNICAL FIELD

The present invention relates to a therapeutic agent for a corneal disease, and more particularly, it relates to a therapeutic agent for a corneal disease applicable to a disorder in the anterior epithelium of cornea, particularly in a formulation of ophthalmic solutions.

BACKGROUND ART

Disorder in the anterior epithelium of cornea can be classified roughly into 4 types, that is, (1) one caused by an inflammation such as infection, (2) hereditary disease, (3) exogenous physical injury and chemical injury caused by chemicals, and (4) nutritional disorder.

Among them, there is a tendency for corneal diseases to increase in recent years due to physical injury accompanied by lacrimal hyposecretion (so-called dry-eye) with the spread of personal computers and contact lens, and those caused by pollinosis, particularly disorder in the anterior epithelium; thus, a drug effective to corneal diseases or disorders in the anterior epithelium of cornea has been demanded.

As drugs recently used in treatment of corneal diseases, artificial tears containing a visco-elastic material such as hyaluronic acid or chondroitin sulfate is known, of which the water-retention effect mainly promotes a cure. There is a limitation, however, in their therapeutic effect, and further it could not be said that they fundamentally cure the corneal disease. A quite new therapeutic agent has been demanded, accordingly.

DISCLOSURE OF INVENTION

Problems to be Solved by the Invention

It is an object of the present invention to find out a drug which is capable of effectively curing and improving a corneal disease increasing in recent years and to provide a therapeutic agent comprising it as an active ingredient.

Means for Solving the Problems

The present inventors have searched for a variety of drugs which have a therapeutic effect on corneal diseases and found that ozagrel has an excellent therapeutic effect on a corneal disease, though ozagrel has been used as an internally administrable medicament for treatment of bronchial asthma or as an injection for improvement of cerebrovascular spasm and its complicated cerebral ischemia occurring after a surgery for subarachnoid hemorrhage. The invention was thus completed.

That is, the present invention provides a therapeutic agent for a corneal disease which comprises ozagrel or a salt thereof as an active ingredient.

The present invention also provides a therapeutic agent for a corneal disease as mentioned above which is in a formulation of ophthalmic solutions and which is particularly applicable to disorders in the anterior epithelium of cornea.

Effect of the Invention

The therapeutic agent of a corneal disease of the present invention has an effect of significantly promoting a cure of corneal diseases, particularly cure of disorders in the anterior epithelium of cornea.

BEST MODE FOR CARRYING OUT THE INVENTION

The corneal disease in the present invention indicates conditions of injured cornea caused by various factors, specifically including keratitis caused by physical/chemical irritation, allergy, bacteria/fungi/virus infections, etc., as well as corneal ulcer, abrasion of the anterior epithelium of cornea (corneal erosion), edema of the anterior epithelium of cornea, corneal burn, corneal corrosion by chemicals, dry-eye, and the like.

The therapeutic agent for a corneal disease of the invention comprises ozagrel or a salt thereof as an active ingredient. The active ingredient, ozagrel or a salt thereof, inhibits the production of thromboxane A2 and exhibits a platelet aggregation-inhibiting effect and an airway contraction inhibiting effect. One of them, i.e., ozagrel sodium ((E)-3-[4-(1H-imidazol-1-ylmethyl)phenyl]acrylic acid sodium salt) has widely been used as an injection for improvement of cerebrovascular spasm and its complicated cerebral ischemia after a surgery for subarachnoid hemorrhage. On the other hand, ozagrel hydrochloride ((E)-3-[p-(1H-imidazol-1-ylmethyl)phenyl]acrylic acid hydrochloride) has widely been used as an internally administrable medicament for treatment of bronchial asthma. It has not yet been known, however, that the ingredient is effective as a therapeutic agent for a corneal disease, particularly in treatment of a disorder of the anterior epithelium of cornea.

In the therapeutic agent for a corneal disease of the present invention, the content of ozagrel or a salt thereof is usually, for example, when ozagrel sodium is used in a liquid preparation such as ophthalmic solution or eyewash, preferably 0.01 w/v % to 3 w/v %, more preferably 0.01 w/v % to 2 w/v %, and most preferably 0.5 w/v % to 1 w/v %.

Alternatively, for example, when ozagrel hydrochloride is used in a liquid preparation such as ophthalmic solution or eyewash, the content is usually about 0.01 w/v % to 3 w/v %, preferably 0.01 w/v % to 2 w/v %, particularly 0.5 w/v % to 1 w/v %.

The therapeutic agent for a corneal disease of the present invention can be formulated into an optional formulation which can be applied to the cornea, and it is desired to usually provide as a form of ophthalmic solution, eyewash, ophthalmic ointment, and the like, in particular as a form of ophthalmic solution.

For example, when the therapeutic agent for a corneal disease of the invention is provided as an ophthalmic solution, it is possible to employ in addition to the active ingredient ozagrel or a salt thereof a variety of optional ingredients including buffer, tonicity agent, solubilizer, surfactant, stabilizer, preservative, pH adjuster, and the like.

The optional ingredients are exemplified specifically by buffer such as potassium dihydrogen phosphate, sodium hydrogen phosphate, boric acid, sodium borate, sodium citrate, sodium acetate, monoethanolamine, trometamol, and the like; tonicity agent such as sodium chloride, potassium chloride, glycerin, glucose, and the like; solubilizer such as ethanol, castor oil, and the like; surfactant such as polysorbate 80, polyoxyethylene hardened castor oil, and the like; stabilizer such as sodium ethylenediaminetetraacetate and the like; preservative such as benzalkonium chloride, benzethonium chloride, chlorobutanol, benzyl alcohol, and the like, and pH adjuster such as hydrochloric acid, sodium hydroxide, and the like.

In addition, the therapeutic agent for a corneal disease of the present invention can be simultaneously used with another type of therapeutic ingredients for a corneal disease of which the action mechanism is considered to be different in order to enhance additively or synergistically the therapeutic effect. The another type of therapeutic ingredients for a corneal disease includes, for example, hyaluronic acid or its salt or chondroitin sulfate or its salt. Those ingredients may be combined with ozagrel or a salt thereof, or may be separately formulated into a single formulation for treatment of a corneal disease so as to use concomitantly.

The therapeutic agent for a corneal disease thus obtained may be applied appropriately to the cornea depending on the type or severity of a corneal disease. In general, a dose of about 0.01 to 0.1 mL for one eye may be administered 3 to 6 times per day.

EXAMPLES

The following Examples and Test Example will illustrate the present invention in more detail. The therapeutic agent for a corneal disease of the invention, however, is not limited by Examples described below, and of course it may be modified in various ways within the scope of the invention as far as the modification does not depart from the gist of the invention.

Example 1

Therapeutic Agent-1 for a Corneal Disease

| (Component) | |
|---|---|
| Ozagrel sodium | 0.5 g |
| Polysorbate 80 | 0.1 g |
| Physiological saline | Balance to total 100 mL |

(Method of Preparation)

Ozagrel sodium (0.5 g) and polysorbate 80 (0.1 g) were dissolved in physiological saline to obtain 100 mL of a therapeutic agent for a corneal disease as an ophthalmic solution.

Example 2

Therapeutic Agent-2 for a Corneal Disease

| (Component) | |
|---|---|
| Ozagrel sodium | 1.0 g |
| Polysorbate 80 | 0.1 g |
| Physiological saline | Balance to total 100 mL |

(Method of Preparation)

Ozagrel sodium (1.0 g) and polysorbate 80 (0.1 g) were dissolved in physiological saline to obtain 100 mL of a therapeutic agent for a corneal disease as an ophthalmic solution.

Test Example (1) Formation of Wound

A matured white rabbit (about 2 kg of body weight) was anesthetized with pentobarbital sodium (0.4 mL/kg) injected into auricular vein; the eyelid was widely opened with an eye speculum, to which 30 μL of benoxil ophthalmic solution was applied to anesthetize the eye surface. Then, a membrane filter (6 mm in diameter) moistened with n-heptanol was placed at the center of rabbit's cornea for one minute to yield corneal injury. After the filter was removed, the eye was washed well with sterilized physiological saline.

In addition, immediately after formation of the wounds, there was no significant difference among groups in the area of wounds; this was confirmed in the same procedure as in observation of cure as mentioned below.

(2) Application of the Preparation

At two, four and six hours after formation of the wound, 100 μL of the therapeutic agents for corneal disease (ophthalmic solution) prepared in Example 1 and Example 2, respectively, were applied to the eye. In this test, physiological saline containing 0.1% polysorbate 80 was used as a control, respectively.

(3) Staining and Observation of Cure

At 24 hours after formation of the wound, 1% aqueous fluorescein solution (50 μL) was applied to the eye for staining. After that, excess fluorescein was washed out with sterilized physiological saline. Subsequently, the cornea was photographed with a digital camera fitted to a photo-slit lamp to observe the status of cure of the wound.

(4) Evaluation

In each experiment, immediately after and 24 hours after the application, the stained area was measured using a image processing software with a label width (5 mm) of eye speculum as a standard, and this was regarded as a wound area. From those results, the cure rate was calculated according to the following formula.

$$\text{Cure rate}(\%) = [1 - (S_B/S_A)] \times 100$$

$S_A$: wound area immediately after formation of wound $S_B$: wound area after application of the preparation Table 1 shows the test results in the therapeutic agent-1 for a corneal disease, and Table 2 shows the test results in the therapeutic agent-2 for a corneal disease, respectively.

TABLE 1

| | Cure Rate (Mean ± S.E. (n = 4)) |
|---|---|
| Control | 57.11 ± 2.68 |
| Therapeutic agent-1 | 66.17 ± 2.54* | t-test
*P < 0.05 vs Control

TABLE 2

| | Cure Rate (Mean ± S.E. (n = 5)) |
|---|---|
| Control | 64.71 ± 1.73 |
| Therapeutic agent-2 | 71.38 ± 1.88* | t-test
*P < 0.05 vs Control

As mentioned above, it was shown that the therapeutic agent for a corneal disease in the present invention has a potent curative effect to a disorder in the anterior epithelium of cornea.

INDUSTRIAL APPLICABILITY

The pharmaceutical preparation of the present invention comprising ozagrel or a salt thereof as an active ingredient has an effect significantly promoting a cure of a corneal disease, particularly, a cure of a disorder in the anterior epithelium of cornea. The pharmaceutical preparation, accordingly, is effective as a novel therapeutic agent for a corneal disease.

What we claim is:

1. A method for treating a corneal disease comprising administering in an ophthalmic solution or eye wash to a patient in need thereof an effective amount of ozagrel or a salt thereof.

2. The method of claim 1, wherein an ozagrel salt is administered.

3. The method of claim 2, wherein the salt is a sodium salt or a hydrochloride salt.

4. The method of claim 1, wherein ozagrel or the salt thereof is present in an amount of 0.01 w/v % to 3 w/v %.

5. The method of claim 1, wherein ozagrel or the salt thereof is present in an amount of 0.01 w/v % to 2 w/v %.

6. The method of claim 1, wherein ozagrel or the salt thereof is present in an amount of 0.5 w/v % to 1 w/v %.

7. The method of claim 1, wherein the ophthalmic solution or eyewash further comprises one or more of a buffer, a tonicity agent, a solubilizer, a surfactant, a stabilizer, a preservative, and a pH adjuster.

8. The method of claim 1, further comprising administering hyaluronic acid, chondroitin sulfate, a salt thereof, or a combination thereof.

9. The method of claim 1, wherein ozagrel or the salt thereof is administered in a dose of 0.01 to 0.1 mL for one eye.

10. The method of claim 9, wherein ozagrel or the salt thereof is administered from 3 to 6 times per day.

11. The method of claim 1, wherein ozagrel or the salt thereof is administered from 3 to 6 times per day.

12. The method of claim 1, wherein said corneal disease is a disorder of the anterior epithelium of the cornea.

13. The method of claim 12, wherein said disorder of the anterior epithelium of the cornea is caused by inflammation.

14. The method of claim 12, wherein said disorder of the anterior epithelium of the cornea is a hereditary disease.

15. The method of claim 12, wherein said disorder of the anterior epithelium of the cornea is an exogenous physical injury.

16. The method of claim 12, wherein said disorder of the anterior epithelium of the cornea is a chemical injury.

17. The method of claim 12, wherein said disorder of the anterior epithelium of the cornea is a nutritional disorder.

* * * * *